United States Patent
Denner et al.

(10) Patent No.: US 9,182,540 B2
(45) Date of Patent: Nov. 10, 2015

(54) DEVICE FOR HOMOGENIZING A LASER-BEAM PROFILE

(71) Applicant: Carl Zeiss Meditec AG, Jena (DE)

(72) Inventors: Rene Denner, Reisdorf (DE); Manfred Dick, Gefell (DE); Jenny Duenger, Jena (DE); Gerald Kunath-Fandrei, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 176 days.

(21) Appl. No.: 13/719,324

(22) Filed: Dec. 19, 2012

(65) Prior Publication Data

US 2013/0170806 A1 Jul. 4, 2013

(30) Foreign Application Priority Data

Dec. 23, 2011 (DE) .......................... 10 2011 122 209

(51) Int. Cl.
| | |
|---|---|
| G02B 6/10 | (2006.01) |
| G02B 6/02 | (2006.01) |
| F21V 8/00 | (2006.01) |
| G02B 27/09 | (2006.01) |
| G02B 27/48 | (2006.01) |
| G02B 6/14 | (2006.01) |
| A61F 9/008 | (2006.01) |
| A61B 18/00 | (2006.01) |
| A61B 18/22 | (2006.01) |

(52) U.S. Cl.
CPC .............. *G02B 6/02* (2013.01); *A61F 9/00821* (2013.01); *A61F 9/00823* (2013.01); *G02B 6/0001* (2013.01); *G02B 6/14* (2013.01); *G02B 27/0994* (2013.01); *G02B 27/48* (2013.01); *A61B 2018/00589* (2013.01); *A61B 2018/2205* (2013.01); *A61F 2009/00863* (2013.01)

(58) Field of Classification Search
None
See application file for complete search history.

(56) References Cited

U.S. PATENT DOCUMENTS

| | | | |
|---|---|---|---|
| 6,672,739 B1 * | 1/2004 | Argyle et al. ................. | 362/259 |
| 6,830,567 B2 | 12/2004 | Schuele et al. | |
| 7,167,630 B2 * | 1/2007 | Eyal et al. ..................... | 385/146 |
| 8,831,396 B1 * | 9/2014 | Price et al. .................... | 385/146 |
| 2012/0069861 A1 * | 3/2012 | Neuberger ....................... | 372/6 |
| 2013/0258336 A1 * | 10/2013 | Ostermeyer et al. .......... | 356/364 |

FOREIGN PATENT DOCUMENTS

| | | |
|---|---|---|
| DE | 3936716 A1 | 5/1991 |
| DE | 10135944 A1 | 2/2003 |

* cited by examiner

*Primary Examiner* — Sung Pak

(74) *Attorney, Agent, or Firm* — Leydig, Voit & Mayer, Ltd.

(57) ABSTRACT

A device for homogenizing a laser-beam profile and a method for focussing and homogenizing a laser beam in laser photocoagulation for coagulating organic tissue, for example in the eye of a living organism.

20 Claims, 3 Drawing Sheets

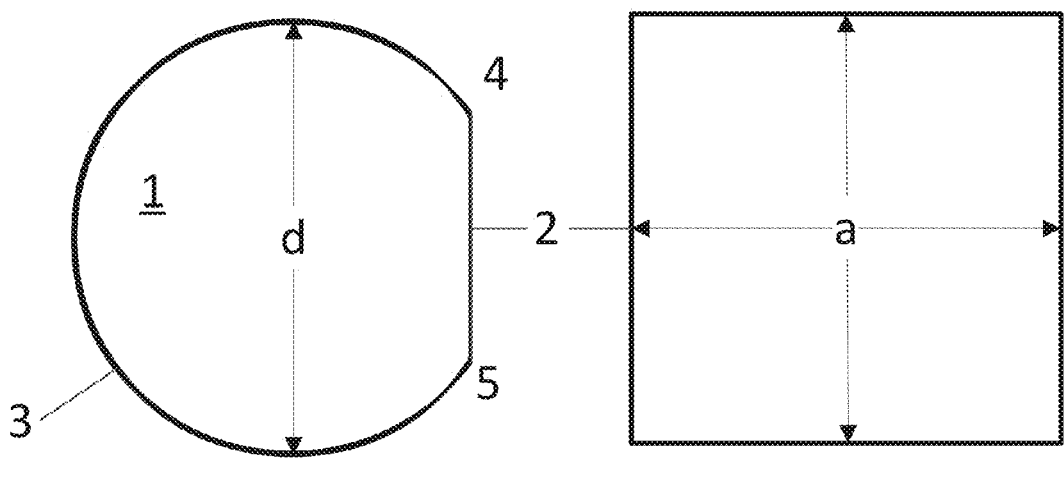
Figure 1                              Figure 2

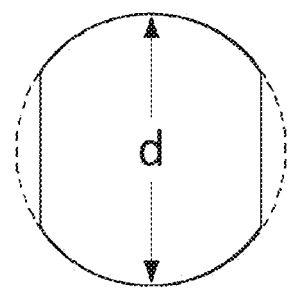
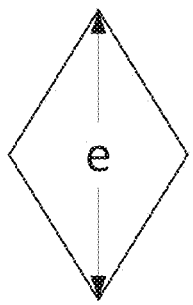
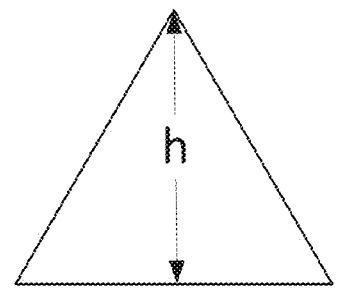
Figure 3　　　　　Figure 4　　　　　Figure 5
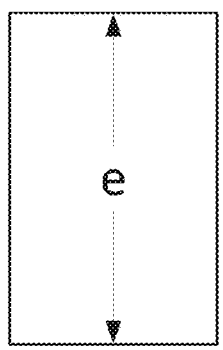
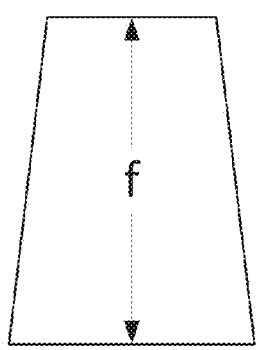
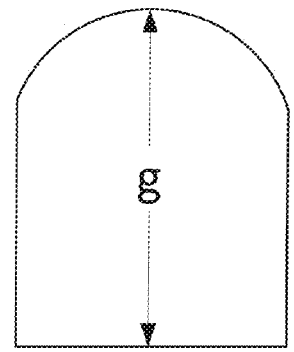
Figure 6　　　　　Figure 7　　　　　Figure 8
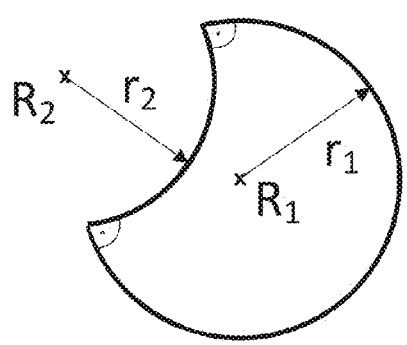
Figure 9

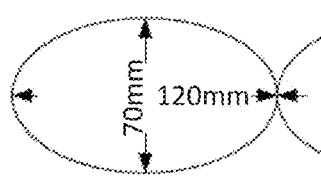
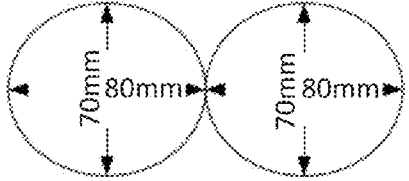
Figure 10                    Figure 11
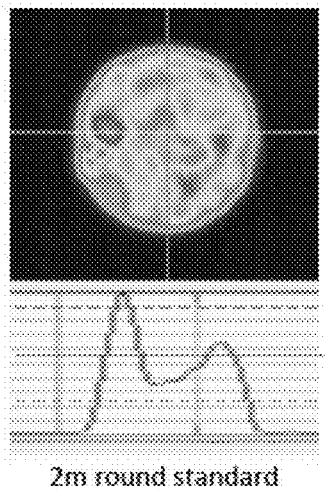
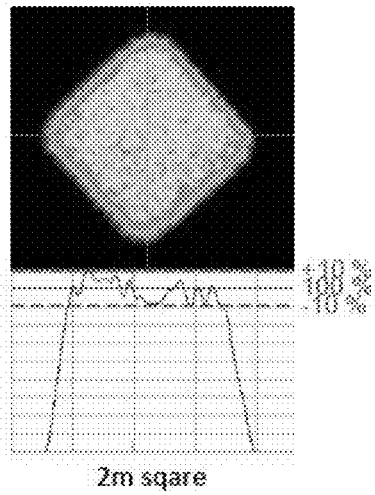
Figure 12                    Figure 13

DEVICE FOR HOMOGENIZING A LASER-BEAM PROFILE

CROSS REFERENCE TO RELATED APPLICATIONS

Priority is claimed to German Patent Application No. DE 10 2011 122209.3, filed on Dec. 23, 2011, the entire disclosure of which is incorporated by reference herein.

FIELD

The invention relates to a device for homogenizing a laser-beam profile. In particular, the invention relates to a device and a method for focussing and homogenizing a laser beam in laser photocoagulation for coagulating organic tissue, for example in the eye of a living organism.

BACKGROUND

A system for laser photocoagulation is known from DE 3936716 A1 and DE 10135944.

A disadvantage of the laser photocoagulators described in the state of the art is that spatial laser-beam profiles with heavy "speckle" occur at the point of impact with the fundus of the eye, which is caused in particular by the inhomogeneous intensity distribution of the transverse mode structure. Inside the laser-beam profile, these inhomogeneities result in significant local thermal elevations (hotspots) during the treatment which far exceed the actual coagulation temperature of approx. 50° C. In standard laser photocoagulation, as a result of the heat conduction into the nerve fibre layer, this leads to a significant increase in pain for the patient and in addition to damage of tissue that is worth preserving.

In addition, because of the spatially inhomogeneous short measurement pulses of a few nanoseconds up to a few microseconds, as a result of the thermal confinement (50 µs), considerable hotspots (>100° C. to 140° C.) occur and thus also cavitation bubbles form inside a light-absorbing tissue layer of the retinal pigment epithelium (RPE).

When these cavitation bubbles collapse, pressure transients form which far exceed the pressure transients, produced by optoacoustics, of the temperature-controlled laser photocoagulation and thus render the actual temperature measurement signal unusable.

An object of the present invention is to overcome the disadvantages known from the state of the art.

SUMMARY

The object can be achieved by a device for homogenizing a laser-beam profile and for focussing a laser spot, comprising an optical waveguide including a fiber core, wherein the edge of the cross-section of the fibre core comprises a straight section.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 1 a schematic view of an optical waveguide with a fibre core cross-section flattened on one side, FIG. 2 an alternative schematic view of an optical waveguide with a square fibre core cross-section, FIG. 3 an alternative schematic view of an optical waveguide with a fibre core cross-section flattened on two sides, FIG. 4 an alternative schematic view of an optical waveguide with a rhombic fibre core cross-section, FIG. 5 an alternative schematic view of an optical waveguide with a triangular fibre core cross-section, FIG. 6 an alternative schematic view of an optical waveguide with a rectangular fibre core cross-section, FIG. 7 an alternative schematic view of an optical waveguide with a trapezoidal fibre core cross-section, FIG. 8 an alternative schematic view of an optical waveguide with a fibre core cross-section flattened on three sides, FIG. 9 an alternative schematic view of an optical waveguide with a crescent-shaped fibre core cross-section, FIG. 10 a schematic view of a figure-of-eight loop, FIG. 11 an alternative schematic view of a figure-of-eight loop from FIG. 9, FIG. 12 a view of the distribution of the homogeneity of the laser-beam profile in the case of a round fibre core and FIG. 13 a view of the distribution of the homogeneity of the laser-beam profile in the case of a square fibre core.

DETAILED DESCRIPTION

A laser-beam profile is preferably an intensity profile within the meaning of an intensity distribution in the cross-section of a laser beam. The fewer regions of a locally elevated intensity there are within the observed cross-section, the more homogeneous the laser-beam profile.

A laser spot is the imaging of the laser light emerging from the fibre core on a plane to be focussed. It is focussed in a target plane, preferably on a retina.

A fibre core is preferably a core running longitudinally inside the fibre. The core is preferably surrounded by a fibre sheath and a protective covering. The core and the sheath preferably have different refractive indices.

Optical waveguides or light conducting cables are preferably cables and wires consisting of light guides and partly assembled with connectors, for the transmission of light. The light guides used, in which the light is guided, are preferably fibres made of quartz glass or polymeric optical fibres made of plastic. They are often also called glass fibre cables, wherein typically a combination of several optical fibres or optical waveguides with integrated mechanical reinforcement for protecting and stabilizing the individual fibres is involved.

A straight section is preferably a substantially straight line that is delimited by two points. It runs continuously and is in a strict geometric sense the shortest route between its two end-points. According to the invention, substantially straight sections with a tolerance can also be used.

Instead of the straight section, preferably convex, concave or other geometries can also be used.

A circular cross-section the outline of which has at least one straight section is called a "flattened" cross-section below.

The flattened fibre core cross-section is preferably a cross-section which is not precisely round, but has the geometry of an arc the two open arc ends of which are connected by a straight line.

As a result of the imaging of the flattened fibre cross-section onto the treatment field, for the first time the attending doctor sees a flattened laser spot in the focal plane and can thus very easily recognize the focal plane through the shape that forms of the image. The attending doctor is thus in a position, using the straight section, to precisely focus the treatment laser beam on the retina.

In addition, as a result of this geometry, for the first time the attending doctor obtains a laser spot the focal plane of which can now be very easily recognized through the sharpness of the corners. The attending doctor is thus in a position, using the corners present, to precisely focus the treatment laser beam on the retina.

This particular geometry of the core surprisingly results in an extremely good homogenization of the identity profile of the laser beam. As a result of the above-mentioned flattening, the helical beams which otherwise circulate essentially around the outside are refracted and thus guided directly through the fibre core, where additional fibre modes are excited. The spikes which otherwise occur with round geometries and which result in local energy elevations and interfere with the sensitive acoustic temperature measurement no longer occur. A homogeneity is thereby produced which also allows acoustic temperature measurements to be carried out for example during a photocoagulation of the retina.

The arc of the flattened cross-section preferably has a radius of from 30 µm-100 µm. The radius is particularly preferably from 40 µm-60 µm. The radius is quite particularly preferably 50 µm.

In a further embodiment, the optical waveguide has straight sections which are linked together and form a polyangular/n-angular fibre core cross-section. Preferably, one end of the straight section is initially connected to the start of the next straight section. The n-angular cross-section of the fibre core is formed as a result of the linking together of a plurality of straight sections.

In a further embodiment, the outline of the cross-section of the fibre core has four straight sections of equal length which form a square fibre core cross-section. The length of the edge (length of the straight section) is preferably 50 µm-100 µm. The length of the edge is particularly preferably 60 µm-80 µm. The length of the edge is quite particularly preferably 50 µm.

By polyangular (n-angular) fibre cross-sections are meant shapes which are for example rhombic, triangular, rectangular, trapezoidal or, in addition to these shapes, also have arc-shaped or curvilinear geometries. Each of the corners ensures an interference with the above-mentioned helical radiation.

The n-angular cross-section preferably has corners for n=1, 2, 3, 4, ..., 12, 16, 20, 24. A monoangular cross-section has only one corner which results for example from one point of intersection of two tangents of an arc. A biangular cross-section has two corners which result for example where a secant intersects with the arc.

In a further embodiment of the invention, sections of the optical waveguide have different fibre cross-sections. Thus different cross-section shapes can be combined with each other in the longitudinal direction of the optical waveguide. For example, a circular cross-section of the optical waveguide can pass into a square cross-section or adjoin it. Furthermore, a square cross-section can also pass into a triangular cross-section or adjoin it.

Fibre cross-sections with flattened, preferably polyangular (n-angular), particularly preferably square, fibre ends are preferably arranged towards the end of the optical waveguide. It is preferred that at least the last 5%, preferably the last 10%, particularly preferably the last 20%, of the total length of the optical waveguide has a flattened, preferably polyangular (n-angular), particularly preferably square, fibre cross-section.

A microoptically active structure is preferably provided on the irradiation surface of the optical waveguide according to the invention. Through such a microoptically active structure, the laser beam is also already directed, upon entry into the optical waveguide, into the centre of the core where it can then excite further fibre modes.

For this, for example the irradiation surface of the optical waveguide is etched, preferably in a hydrofluoric acid solution, particularly preferably in the developing vapour phase of a 60% hydrofluoric acid solution.

The residence time of the optical waveguide in the etching medium is preferably 2 to 8 minutes and particularly preferably 5 minutes. A sufficient removal of material at the fibre ends can thereby take place and the microoptically active surface can develop adequately without the fibre ends being made unusable for later coupling of light.

The microoptically active structure is preferably produced by rough grinding of the irradiation surface of the optical waveguide with fibre sandpaper.

The microoptical structure is preferably applied such that the limiting angle of the total reflection or the limiting aperture of the fibres is not exceeded. This is achieved through the choice of the structuring of the fibre coupling side relative to the structure depth, structure breadth and refractive or diffractive optical effect such that the transmission losses from the fibre core to the fibre sheath of the step-index fibre or also graded-index fibre are kept in a low percent range.

During the coupling, the aperture of the laser beam to be coupled is preferably chosen to be less than the limiting aperture of the fibre in order to fully utilize the limiting aperture of the fibre with the help of the microoptical structure on the fibre surface.

In a further embodiment of the invention, the optical waveguide for homogenizing the laser-beam profile is laid/arranged in a specific pattern. As a result of different radii of curvature of the light beam guides in the pattern laid, there is a good mix of modes within the optical waveguide. The patterns are preferably loops; the loops are preferably formed as figure-of-eight loops. The figure-of-eight loop has roughly the shape of a horizontal eight.

The optical waveguide is preferably laid in several figure-of-eight loops of one size, particularly preferably in several figure-of-eight loops of different sizes.

The pattern preferably has at least one figure-of-eight loop, wherein the loop size measures 70 mm×80 mm or 100 mm×160 mm.

The pattern particularly preferably has at least two different figure-of-eight loops, wherein one loop size measures 70 mm×80 mm and the other loop size measures 100 mm×160 mm.

The length of the optical waveguide should preferably be chosen long enough to reach the coherence length of the laser used, or even exceed it, in order to guarantee a sufficient mix of modes.

The optical waveguide is preferably at least 2 meters long, further preferably up to 10 meters long, particularly preferably at least 50 meters long.

The device preferably has an external bending mechanism for bending the optical waveguide used. The bending radius of the optical waveguide can be changed by the external bending mechanism. The bending radius is continuous changed, with the result that the mode pattern continuously changes, which results in a temporal homogenization of the laser-beam profile during the treatment of the patient.

The bending mechanism is preferably formed as a mechanical vibration system within the meaning of spring-mass system, magnetic drive and/or connecting-rod drive, but particularly preferably as a piezo actuator.

The spring-mass system describes a device for determining the deformation behaviour of objects. It can be applied both to flat and to three-dimensional objects.

A connecting-rod drive is a drive in which a connecting rod (con rod, slide rod, driving rod) in a crank drive forms the connection between the crankshaft or the crankpin and the part moving in a straight line.

Piezo actuators are used to deform materials upon application of an electrical voltage. As result of the application of an electrical voltage, the piezo actuator executes a mechanical movement (so-called inverse piezo effect).

The bending mechanism is preferably set up to bend the optical waveguide at a repetition rate of from 1 to 10 kHz, preferably from 3 to 8 kHz, particularly preferably of 5 kHz.

In a further embodiment of the invention, the imaging system of the fibre coupling can be designed such that the numerical aperture of the fibre can be utilized to the maximum. This results in the excitation of as many fibre modes as possible and thus likewise in laser beam homogenization.

In a further embodiment of the invention, it is provided to use the device in a laser photocoagulation in the eye of a living organism.

In the two following examples (Examples 1 and 2), values of a round fibre according to the state of the art and a square fibre according to the present invention are compared and recorded in tables.

Accordingly, in Example 1 different values are shown for energy per surface area (=energy density) [in $mJ/cm^2$] for example for a round fibre, which follow for corresponding pulse energy [in µJ] and spot size [in µm]. The length of the optical waveguide is 2 meters here. A frequency-doubled Nd:YAG laser (wavelength 532 nm) with a pulse length of approx. 250 ns was used.

The regions in which the energy per surface area is >250 $mJ/cm^2$ and in which the formation of cavitation bubbles is to be expected.

| round fibres | | | | | | | |
|---|---|---|---|---|---|---|---|
| pulse energy | spot size [µm] | | | | | | |
| [µJ] | 50 | 100 | 200 | 300 | 500 | 1000 | |
| 2 | 415.8 | 203.7 | 50.9 | 22.6 | 8.1 | 2.0 | energy/ |
| 3 | 623.6 | 305.6 | 76.4 | 34.0 | 12.2 | 3.1 | surface |
| 4 | 831.5 | 407.4 | 101.9 | 45.3 | 16.3 | 4.1 | area |
| 5 | 1039.4 | 509.3 | 127.3 | 56.6 | 20.4 | 5.1 | [$mJ/cm^2$] |
| 6 | 1247.3 | 611.2 | 152.8 | 67.9 | 24.4 | 6.1 | |
| 7 | 1455.1 | 713.0 | 178.3 | 79.2 | 28.5 | 7.1 | |
| 8 | 1663.0 | 814.9 | 203.7 | 90.5 | 32.6 | 8.1 | |
| 9 | 1870.9 | 916.7 | 229.2 | 101.9 | 36.7 | 9.2 | |
| 10 | 2078.8 | 1018.6 | 254.6 | 113.2 | 40.7 | 10.2 | |
| 11 | 2286.6 | 1120.5 | 280.1 | 124.5 | 44.8 | 11.2 | |
| 12 | 2494.5 | 1222.3 | 305.6 | 135.8 | 48.9 | 12.2 | |

EXAMPLE 1

In Example 2, different values are shown for energy per surface area [in $mJ/cm^2$] for example for a square fibre, which follow for corresponding pulse energy [in µJ] and spot size [in µm]. The length of the optical waveguide is also 2 meters here.

There are no values for which the energy per surface area is >250 $mJ/cm^2$. Thus formation of cavitation bubbles is not to be expected.

| square fibres | | | | | | | |
|---|---|---|---|---|---|---|---|
| pulse energy | spot size [µm] | | | | | | |
| [µJ] | 70 | 100 | 200 | 300 | 500 | 1000 | |
| 2 | 40.8 | 20.0 | 5.0 | 2.2 | 0.8 | 0.2 | energy/ |
| 3 | 61.2 | 30.0 | 7.5 | 3.3 | 1.2 | 0.3 | surface |
| 4 | 81.6 | 40.0 | 10.0 | 4.4 | 1.6 | 0.4 | area |
| 5 | 102.0 | 50.0 | 12.5 | 5.6 | 2.0 | 0.5 | [$mJ/cm^2$] |
| 6 | 122.4 | 60.0 | 15.0 | 6.7 | 2.4 | 0.6 | |
| 7 | 142.9 | 70.0 | 17.5 | 7.8 | 2.8 | 0.7 | |
| 8 | 163.3 | 80.0 | 20.0 | 8.9 | 3.2 | 0.8 | |
| 9 | 183.7 | 90.0 | 22.5 | 10.0 | 3.6 | 0.9 | |
| 10 | 204.1 | 100.0 | 25.0 | 11.1 | 4.0 | 1.0 | |
| 11 | 224.5 | 110.0 | 27.5 | 12.2 | 4.4 | 1.1 | |
| 12 | 244.9 | 120.0 | 30.0 | 13.3 | 4.8 | 1.2 | |

EXAMPLE 2

Thus with the square fibre an improved homogeneity of the intensity distribution is achieved and disadvantages as a result of the formation of cavitation bubbles were avoided.

In addition to the homogenization of a laser beam, an improvement also occurs in the focussability of the laser beam during the laser photocoagulation in the eye of a living organism as a result of the use of a corresponding optical waveguide.

The present invention proposes a device for homogenizing a laser-beam profile inside a laser photocoagulator to avoid local hotspots inside the retinal area to be treated, which simultaneously creates a flexible connection between photo-coagulation laser and the associated applicator (preferably a laser slit lamp) and provides a spot diameter of ≥50 µm at the end such that it can be imaged 1:1 into the treatment field onto the retina of the patient.

At the same time, it is ensured that the treatment laser can be focussed precisely into the treatment field onto the retina of the patient.

FIG. 1 shows a schematic view of an optical waveguide with a "flattened" fibre core cross-section. The fibre core cross-section (1) of the optical waveguide has a circular geometry (3) with diameter (d) which is interrupted by a straight section (2). (d) is for example 50 µm. The straight section (2) is formed as a secant. The secant connects the two arc ends (points (4, 5)) of the circular base body; two corners format points (4) and (5). The surface area of the "flattened" fibre core cross-section is reduced as a result of the flattening to approx. 90% of the surface area of the full circle.

As a result of the above-mentioned flattening, the helical beams which otherwise circulate essentially around the outside are refracted and thus guided directly through the fibre core, where additional fibre modes are excited.

This particular geometry of the core results in an extremely good homogenization of the identity profile of the laser beam.

As a result of the imaging of the flattened fibre cross-section onto the treatment field, for the first time the attending doctor sees a flattened laser spot in the focal plane and can thus very easily recognize the focal plane through the shape that forms of the image. The doctor is thus in a position, using the straight section, to precisely focus the treatment laser beam on the retina.

In addition, as a result of this geometry, for the first time the attending doctor obtains a laser spot the focal plane of which can now be very easily recognized through the sharpness of the corners. The attending doctor is thus in a position, using the corners present, to precisely focus the treatment laser beam on the retina.

The same also applies to the further alternative embodiments, shown in FIGS. 2 to 9, of a fibre core cross-section of FIG. 1. The invention is not limited to these cross-sections.

FIG. 2 shows an alternative schematic view of an optical waveguide with a square fibre core cross-section. The fibre core cross-section of the optical waveguide has an edge length (a). The edge length corresponds to the length (2) of the straight section. The edge length is for example 70 µm.

FIG. 3 shows an alternative schematic view of an optical waveguide with a fibre core cross-section flattened on two sides. The diameter of the circular part of the cross-section (d) is for example 50 µm. The surface area of the fibre core cross-section "flattened" on two sides is reduced as a result of the flattening to approx. 80% of the surface area of the full circle.

FIG. 4 shows an alternative schematic view of an optical waveguide with a rhombic fibre core cross-section with a diagonal length (e) which is for example 70 µm.

FIG. 5 shows an alternative schematic view of an optical waveguide with a triangular fibre core cross-section. The sides of the triangle are equilateral, wherein the triangle height (h) is for example 50 µm. An isosceles triangle is alternatively conceivable (not shown).

FIG. 6 shows an alternative schematic view of an optical waveguide with a rectangular fibre core cross-section, wherein the longest side (e) is for example 70 µm.

FIG. 7 shows an alternative schematic view of an optical waveguide with a trapezoidal fibre core cross-section, wherein the trapezium height (f) is for example 70 µm.

FIG. 8 shows an alternative schematic view of an optical waveguide with a fibre core cross-section flattened on three sides, wherein the height (g) is for example 70 µm.

FIG. 9 shows an alternative schematic view of an optical waveguide with a crescent-shaped fibre core cross-section, wherein the circular part with the centre $R_1$ of the cross-section has the radius ($r_1$). The indentation with the centre $R_2$ has the radius ($r_2$). The geometry of the two interconnecting circular shapes produces corners which enclose a right angle.

FIG. 10 shows a schematic view of a loop. The loop is formed as a figure-of-eight loop and consists of two oval part-elements. The dimensions of the part-elements are identical, wherein their height is given as 100 mm and their breadth as 160 mm.

FIG. 11 shows an alternative schematic view of a figure-of-eight loop with different dimensions. The figure-of-eight loop likewise consists of two oval part-elements. The dimensions of the part-elements are identical, wherein their height is given as 70 mm and their width as 80 mm.

FIG. 12 and FIG. 13 show a representation of the distribution of the homogeneity of the laser-beam profile of a round or a square fibre core for a length of the waveguide of 2 meters in each case.

As shown in FIG. 12, the homogeneity of the laser-beam profile for a 2-meter long round fibre core according to the state of the art is usually no more than ±50%.

This leads, particularly with smaller spot sizes of ≤100 µm, to energy densities of ≥250 mJ/cm² and thus to the undesired formation of cavitation bubbles in the optoacoustic online temperature measurement during laser photocoagulation (cf. Example 1 above).

As shown in FIG. 13 using a 2-meter long square fibre core, a homogeneity of the laser-beam profile of ≤±20%, better still ≤±10%, is achieved in order to ensure energy densities of well below 250 mJ/cm² and thus avoid the undesired formation of cavitation bubbles.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the attached claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise.

The invention claimed is:

1. A device for homogenizing a laser-beam profile and for focussing a laser spot on a target plane, the device comprising:
   an optical waveguide including a fiber core,
     wherein an edge of a cross-section of the fiber core comprises a straight section, the cross-section being disposed at an end of the optical waveguide such that the laser spot comprises a corresponding straight section on the target plane.

2. The device of claim 1, wherein the cross-section comprises a plurality of straight sections which are linked together and form an n-angular fiber core cross-section.

3. The device of claim 1, further comprising:
   a microoptically active structure provided on an irradiation surface of the optical waveguide.

4. The device of claim 1, wherein the optical waveguide is arranged in a specific pattern.

5. The device of claim 4, wherein the pattern comprises a loop.

6. The device of claim 5, wherein the loop has a loop size measuring 70 mm×80 mm.

7. The device of claim 1, further comprising:
   an external bending mechanism configured to bend the optical waveguide.

8. The device of claim 7, wherein the external bending mechanism is a mechanical vibration system comprising at least one of a spring-mass system, magnetic drive, connecting-rod drive, and a piezo actuator.

9. The device of claim 7, wherein the bending mechanism is configured to bend the optical waveguide at a repetition rate of from 1 to 10 kHz.

10. The device of claim 2, wherein the straight sections form a square fiber core cross-section.

11. The device of claim 5, wherein the loop has a loop size measuring 100 mm×160 mm.

12. The device of claim 8, wherein the external bending mechanism comprises a spring-mass system.

13. The device of claim 8, wherein the external bending mechanism comprises a magnetic drive.

14. The device of claim 8, wherein the external bending mechanism comprises a connecting-rod drive.

15. The device of claim 8, wherein the external bending mechanism comprises a piezo actuator.

16. The device of claim 8, wherein the external bending mechanism comprises a spring-mass system and a magnetic drive.

17. The device of claim 8, wherein the external bending mechanism comprises a spring-mass system and a connecting-rod drive.

18. The device of claim 8, wherein the external bending mechanism comprises a spring-mass system and a piezo actuator.

19. The device of claim 8, wherein the external bending mechanism comprises a magnetic drive and a connecting-rod drive.

20. The device of claim 8, wherein the external bending mechanism comprises a magnetic drive and a piezo actuator.

\* \* \* \* \*